US010551276B2

(12) United States Patent
Clark et al.

(10) Patent No.: US 10,551,276 B2
(45) Date of Patent: Feb. 4, 2020

(54) VEHICLE COOLANT FLOW AND COOLANT QUALITY SENSOR ASSEMBLY

(71) Applicants: David A. Clark, Madison, AL (US); Mengying Luo, Huntsville, AL (US)

(72) Inventors: David A. Clark, Madison, AL (US); Mengying Luo, Huntsville, AL (US)

(73) Assignee: Electricfil Corporation, Elkmont, AL (US)

( * ) Notice: Subject to any disclaimer, the term of this patent is extended or adjusted under 35 U.S.C. 154(b) by 170 days.

(21) Appl. No.: 15/831,728

(22) Filed: Dec. 5, 2017

(65) Prior Publication Data

US 2019/0170612 A1  Jun. 6, 2019

(51) Int. Cl.
*G01M 15/05* (2006.01)
*G01F 1/24* (2006.01)
*G01F 1/58* (2006.01)
*G01N 25/00* (2006.01)

(52) U.S. Cl.
CPC ............... *G01M 15/05* (2013.01); *G01F 1/24* (2013.01); *G01F 1/586* (2013.01); *G01F 1/588* (2013.01); *G01N 25/00* (2013.01); *F01P 2025/06* (2013.01); *F01P 2025/08* (2013.01)

(58) Field of Classification Search
CPC .......... G01M 15/05; G01F 1/588; G01F 1/24; G01F 1/586; F01P 2025/08; F01P 2025/06; F01P 2031/20; F02D 41/22
See application file for complete search history.

(56) References Cited

U.S. PATENT DOCUMENTS

| 6,745,995 | B2* | 6/2004 | Hu | F01P 7/167 |
| | | | | 123/41.08 |
| 6,948,361 | B2* | 9/2005 | Popielas | G01F 1/692 |
| | | | | 73/204.22 |
| 7,270,090 | B2* | 9/2007 | Surnilla | F01P 7/048 |
| | | | | 123/41.02 |
| 7,341,097 | B2* | 3/2008 | Darby | F01P 11/0276 |
| | | | | 137/551 |
| 7,762,313 | B2* | 7/2010 | Darby | F01P 11/0276 |
| | | | | 137/551 |
| 7,848,902 | B2* | 12/2010 | Zettel | G01F 1/696 |
| | | | | 123/254 |
| 9,010,141 | B2* | 4/2015 | Harrington | F28D 1/0246 |
| | | | | 62/259.2 |
| 9,636,997 | B2* | 5/2017 | Kolhouse | B60K 11/085 |
| 9,827,824 | B2* | 11/2017 | Enomoto | B60H 1/00878 |
| 9,994,087 | B2* | 6/2018 | Enomoto | F25B 25/005 |
| 10,211,493 | B2* | 2/2019 | Janarthanam | B60L 58/26 |
| 10,221,755 | B2* | 3/2019 | Garraway | F01P 7/04 |

(Continued)

*Primary Examiner* — Freddie Kirkland, III
(74) *Attorney, Agent, or Firm* — Clements Bernard Walker; Christopher L. Bernard; Richard A. Walker

(57) ABSTRACT

A vehicle coolant flow and coolant quality sensor assembly for use in an internal combustion engine (ICE) vehicle, a hybrid vehicle, or an electric vehicle. The coolant flow sensor includes a dual coil magnetic flow meter or the like for measuring coolant flow rate and the coolant quality sensor includes a sealed hot wire anemometer or the like and an integrated temperature sensor or the like for measuring coolant quality (e.g., ability to absorb heat) and coolant temperature, respectively. The various sensors are disposed in an integrated housing through which coolant is transported.

20 Claims, 4 Drawing Sheets

(56) References Cited

U.S. PATENT DOCUMENTS

| | | | |
|---|---|---|---|
| 2002/0179165 A1* | 12/2002 | Hu | F01P 7/167 |
| | | | 137/875 |
| 2004/0144169 A1* | 7/2004 | Popielas | G01F 1/692 |
| | | | 73/200 |
| 2005/0000300 A1* | 1/2005 | Zingg | G01F 1/586 |
| | | | 73/861.15 |
| 2015/0217622 A1* | 8/2015 | Enomoto | B60H 1/00878 |
| | | | 165/42 |
| 2015/0333379 A1* | 11/2015 | Janarthanam | B60L 58/26 |
| | | | 429/61 |
| 2018/0073418 A1* | 3/2018 | Bonkoski | F01P 11/16 |

* cited by examiner

VEHICLE COOLANT FLOW AND COOLANT QUALITY SENSOR ASSEMBLY

FIELD OF THE INVENTION

The present invention relates generally to a vehicle coolant flow and coolant quality sensor assembly for use in an internal combustion engine (ICE) vehicle, a hybrid vehicle, or an electric vehicle. More specifically, the coolant flow sensor includes a dual coil magnetic flow meter or the like for measuring coolant flow rate and the coolant quality sensor includes a sealed hot wire anemometer or the like and an integrated temperature sensor or the like for measuring coolant quality (e.g., ability to absorb heat) and coolant temperature, respectively.

BACKGROUND OF THE INVENTION

Vehicle cooling and thermal management systems are indispensable in modern ICE vehicles, hybrid vehicles, and electric vehicles. For example, a typical electric vehicle utilizes up to four radiators; one for the motor, one for the automatic transmission fluid, one for the battery pack, and one for the high power electronics. All of these components generate a great deal of heat, during both operation and battery charging. If a vehicle cooling and thermal management system fails, a runaway overheating event can occur, badly damaging or even destroying a vehicle and potentially harming its operator and/or passengers.

Multiple factors may contribute to the failure of a vehicle cooling and thermal management system, such as the breakdown of a coolant pump, a coolant leak, an improper coolant mixture, etc. Thus, temperature sensors are typically used to monitor the condition of such systems, with an operator being alerted to a dangerous spike in coolant temperature (e.g., due to a coolant flow and/or quality problem) that could jeopardize an engine, a motor, a transmission, batteries, high power electronics, etc. Disadvantageously, by the time coolant temperature has risen enough to trigger such an operator alert, permanent damage to such components may have already occurred.

Thus, what is still needed in the art is a vehicle coolant flow and coolant quality sensor assembly that does more than simply monitor coolant temperature.

BRIEF SUMMARY OF THE PRESENT INVENTION

In various exemplary embodiments, the present invention provides a vehicle coolant flow and coolant quality sensor assembly for use in an ICE vehicle, a hybrid vehicle, or an electric vehicle. More specifically, the coolant flow sensor includes a dual coil magnetic flow meter or the like for measuring coolant flow rate and the coolant quality sensor includes a sealed hot wire anemometer or the like and an integrated temperature sensor or the like for measuring coolant quality (e.g., ability to absorb heat) and coolant temperature, respectively. By combining these various measurements, an earlier and more accurate picture of coolant flow and quality, and therefore effectiveness, can be derived.

In one exemplary embodiment, the present invention provides a vehicle coolant flow and coolant quality sensor assembly, including: a housing defining a coolant flow channel communicating coolant from a first port to a second port; a coolant flow sensor disposed at least partially within the coolant flow channel and contacting the coolant, wherein the coolant flow sensor is operable for measuring flow of the coolant; and a coolant quality sensor disposed at least partially within the coolant flow channel and contacting the coolant, wherein the coolant quality sensor is operable for measuring ability to absorb heat of the coolant. The vehicle coolant flow and coolant quality sensor assembly further includes a coolant temperature sensor disposed at least partially within the coolant flow channel and contacting the coolant, wherein the coolant temperature sensor is operable for measuring temperature of the coolant. The coolant flow sensor includes a dual coil magnetic flow meter. The coolant quality sensor includes a sealed hot wire anemometer. The vehicle coolant flow and coolant quality sensor assembly still further includes a printed circuit board including one or more of a microcontroller and a transceiver coupled to one or more of the coolant flow sensor and the coolant quality sensor. The vehicle coolant flow and coolant quality sensor assembly still further includes an electronic connector coupled to the printed circuit board. The vehicle coolant flow and coolant quality sensor assembly still further includes a sealing member disposed about one or more of the first port and the second port. The housing is disposed in a cooling and thermal management system of one of an internal combustion engine (ICE) vehicle, a hybrid vehicle, and an electric vehicle. The vehicle coolant flow and coolant quality sensor assembly is used to monitor coolant used to cool one or more of an engine, a motor, a transmission, a battery pack, and high power electronics. The vehicle coolant flow and coolant quality sensor assembly is operable for alerting a user to one or more of coolant flow below a predetermined threshold, coolant ability to absorb heat below a predetermined threshold, and coolant temperature above a predetermined threshold.

In another exemplary embodiment, the present invention provides a method for providing a vehicle coolant flow and coolant quality sensor assembly, including: providing a housing defining a coolant flow channel communicating coolant from a first port to a second port; providing a coolant flow sensor disposed at least partially within the coolant flow channel and contacting the coolant, wherein the coolant flow sensor is operable for measuring flow of the coolant; providing a coolant quality sensor disposed at least partially within the coolant flow channel and contacting the coolant, wherein the coolant quality sensor is operable for measuring ability to absorb heat of the coolant; and disposing the housing in a cooling and thermal management system of a vehicle. The method further includes providing a coolant temperature sensor disposed at least partially within the coolant flow channel and contacting the coolant, wherein the coolant temperature sensor is operable for measuring temperature of the coolant. The coolant flow sensor includes a dual coil magnetic flow meter. The coolant quality sensor includes a sealed hot wire anemometer. The method still further includes providing a printed circuit board including one or more of a microcontroller and a transceiver coupled to one or more of the coolant flow sensor and the coolant quality sensor. The method still further includes providing an electronic connector coupled to the printed circuit board. The method still further includes providing a sealing member disposed about one or more of the first port and the second port. The housing is disposed in the cooling and thermal management system of one of an internal combustion engine (ICE) vehicle, a hybrid vehicle, and an electric vehicle. The vehicle coolant flow and coolant quality sensor assembly is used to monitor coolant used to cool one or more of an engine, a motor, a transmission, a battery pack, and high power electronics. The vehicle coolant flow and coolant quality sensor assembly is operable for alerting a user to one or more of coolant flow below a predetermined threshold, coolant ability to absorb heat below a predetermined threshold, and coolant temperature above a predetermined threshold.

BRIEF DESCRIPTION OF THE DRAWINGS

The present invention is illustrated and described herein with reference to the various drawings, in which like reference numbers are used to denote like assembly components/method steps, as appropriate, and in which.

DETAILED DESCRIPTION OF THE INVENTION

Figure 1:
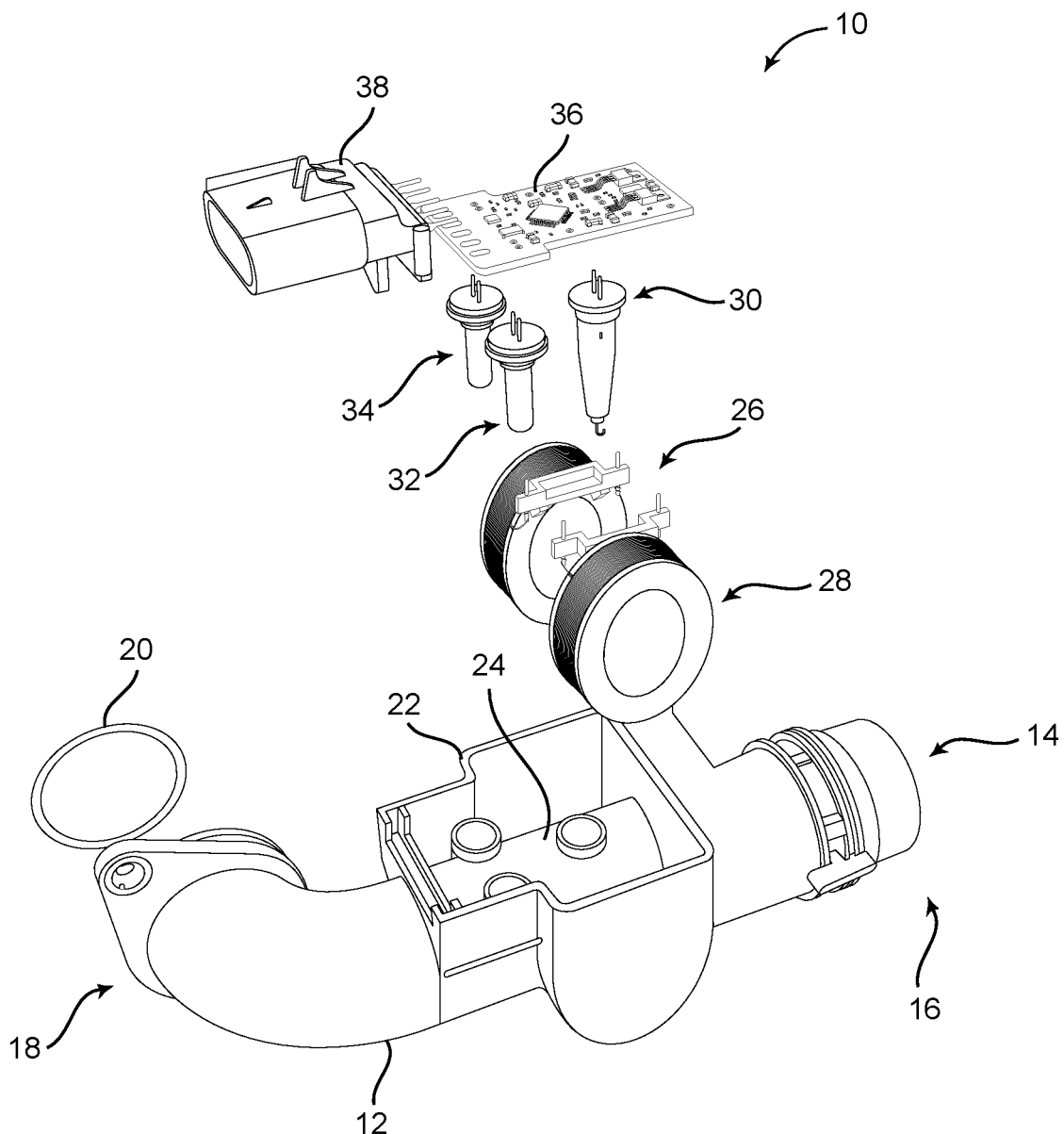
FIG. 1 is a perspective view of one exemplary embodiment of the vehicle coolant flow and coolant quality sensor assembly of the present invention in an exploded configuration.
Figure 2:
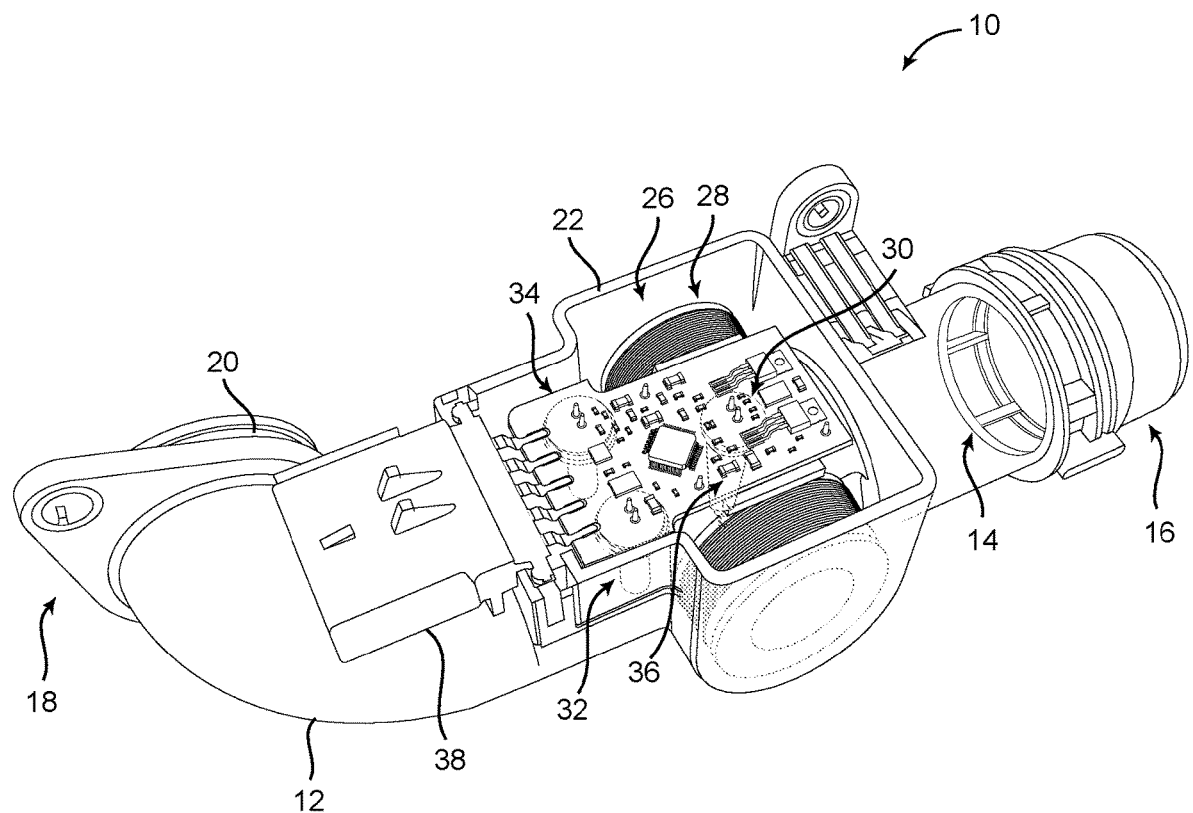
FIG. 2 is a perspective view of one exemplary embodiment of the vehicle coolant flow and coolant quality sensor assembly of the present invention in a partially transparent configuration.
Figure 3:
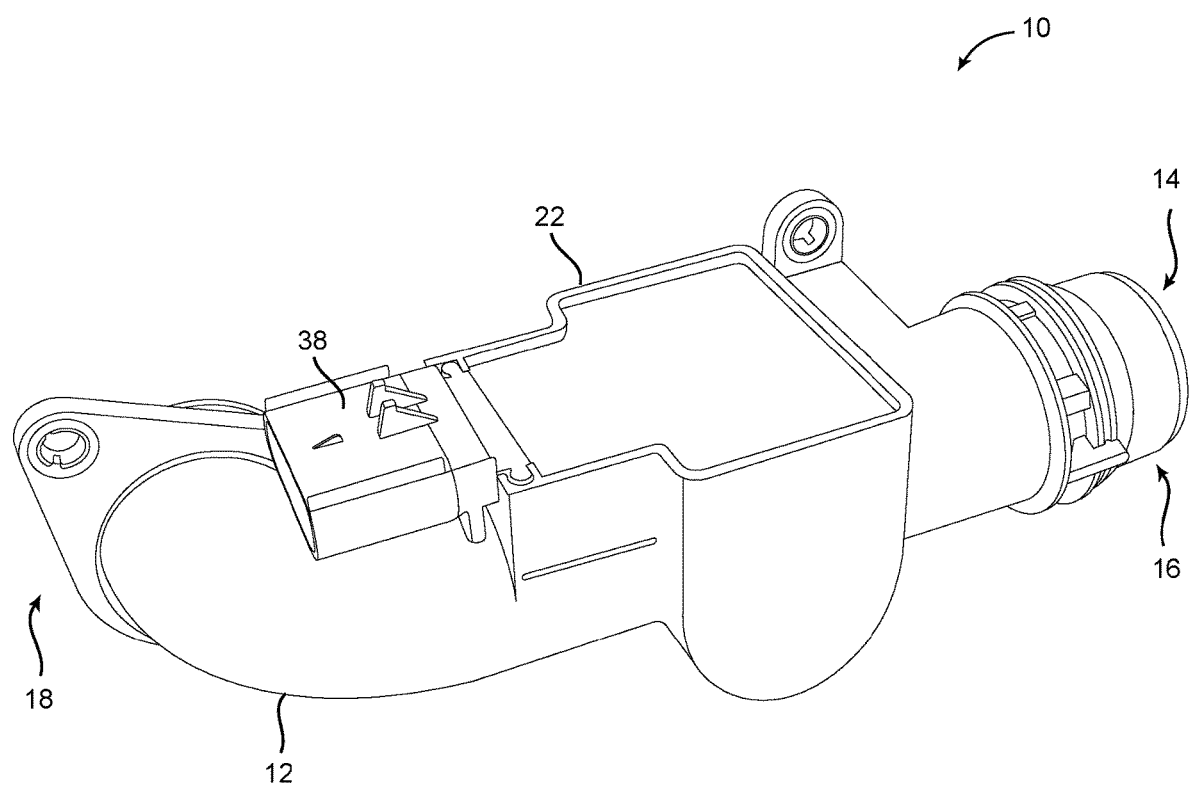
FIG. 3 is a perspective view of one exemplary embodiment of the vehicle coolant flow and coolant quality sensor assembly of the present invention in an assembled configuration.
Figure 4:
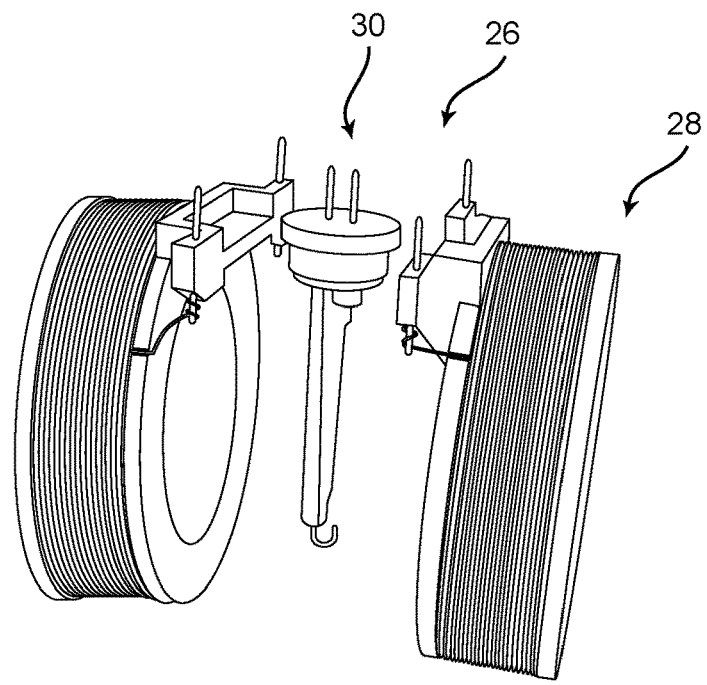
FIG. 4 is a perspective view of one exemplary embodiment of the coolant flow sensor including a dual coil magnetic flow meter or the like for measuring coolant flow rate and the coolant quality sensor including a sealed hot wire anemometer or the like and an integrated temperature sensor or the like for measuring coolant ability to absorb heat and coolant temperature, respectively, as well a printed circuit board incorporating a microcontroller and a transceiver.
Figure 4:
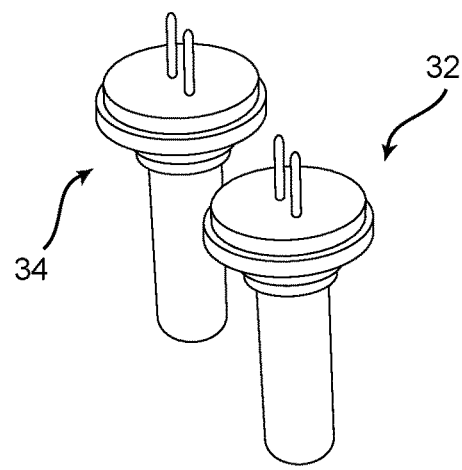
Figure 4:
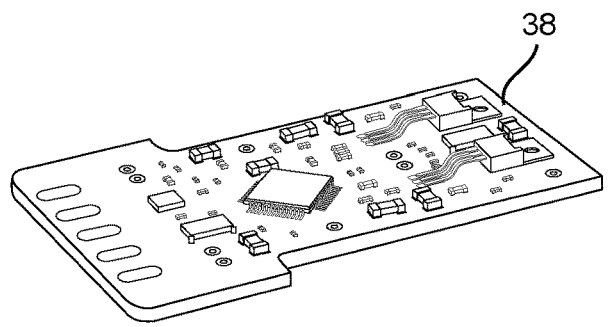

Referring now specifically to FIGS. 1-3, in one exemplary embodiment, the vehicle coolant flow and coolant quality sensor assembly 10 of the present invention includes a housing 12 that defines a coolant flow channel 14 that communicates coolant from a first port 16 to a second port 18. In this respect, the housing 12 acts as a part of a conventional coolant system of a vehicle. The housing 12 may have a conventional coolant system attachment at the first port 16 and an elbow, flange, and/or conventional coolant system attachment at the second port 18, for example, both utilizing O-ring sealing members 20 or the like, as appropriate for providing leak free fluid transport. The center section of the housing 12 includes a widened sensor receiving portion 22 for receiving the various sensors described in greater detail herein below. Within the widened sensor receiving portion 22, the coolant flow channel 14 includes a plurality of sensor ports 24 through which at least a portion of each of the various sensors protrudes into the associated coolant flow such that measurements may be taken.

Referring now specifically to FIGS. 1-4, in one exemplary embodiment, the coolant flow sensor utilized includes a dual coil magnetic flow meter 26 for measuring coolant flow rate. The dual coil magnetic flow meter 26 includes a pair of magnetic coils 28 disposed on opposed sides of the coolant flow channel 14 within conformal receptacles of the widened sensor receiving portion 22 of the housing 12. An electrode 30 is disposed between the pair of magnetic coils 28 and protrudes partially into the coolant flow through one of the sensor ports 24 manufactured into the coolant flow channel 14. Advantageously, this type of flow sensor is ideal for use with a fluid like coolant. The flow sensor is disposed largely outside of the fluid flow and does not disturb or restrict the fluid flow under measurement. There are no moving parts, eliminating wear and tear concerns. The flow sensor measures volume flow, meaning that the measurement is insensitive to changes in fluid viscosity, density, temperature, pressure, etc. The working principle of the flow sensor is based on Faraday's law of electromagnetic induction. According to Faraday's law, when a conductive fluid flows through a magnetic field, an electromotive force proportional to the volume flow is generated between the pair of electrodes, which is perpendicular to the flow direction and the magnetic field. The amplitude of the electromotive force can be expressed as:

$$E = kBDv \qquad (1)$$

Where E is the induced electric potential, k is a constant, B is the magnetic flux density, D is the inner diameter of the measuring tube, and v is the average velocity of the fluid in the axial direction of the electrode cross-section inside the measuring tube. It will be readily apparent to those of ordinary skill in the art, however, that other suitable flow sensors may also be utilized equally. For example, a rotating impellor, pressure differential, ultrasonic, or other flow sensor may be utilized.

The coolant quality sensor utilized includes a sealed hot wire anemometer 32 for measuring coolant flow/quality. In general, hot wire anemometers use a very fine wire (on the order of several micrometers in diameter) electrically heated to some temperature above ambient. Fluid flowing past the wire cools the wire. As the electrical resistance of most metals is dependent upon the temperature of the metal (tungsten is a popular choice for hot wires, for example), a relationship can be obtained between the resistance of the wire and the fluid flow speed, viscosity, ability to absorb heat, etc. Hot wire devices can be further classified as constant current anemometers (CCAs), constant voltage anemometers (CVAs), or constant temperature anemometers (CTAs). The voltage output from these anemometers is thus the result of some sort of circuit within the device trying to maintain the specific variable (current, voltage, or temperature) constant, following Ohm's law. Additionally, pulse-width modulation (PWM) anemometers are also used, wherein the velocity is inferred by the time length of a repeating pulse of current that brings the wire up to a specified resistance and then stops until a threshold "floor" is reached, at which time the pulse is sent again. Hot wire anemometers, while extremely delicate, have extremely high frequency response and fine spatial resolution as compared to other measurement methods, and as such are almost universally employed for the detailed study of turbulent flows, or any flow in which rapid velocity fluctuations are of interest. It will be readily apparent to those of ordinary skill in the art, however, that other suitable flow/quality sensors may also be utilized equally.

The coolant temperature sensor utilized includes one of those known to ordinary skill in the art, such as an integrated coolant temperature sensor 34. As the sensor's temperature changes, its resistance changes accordingly. Depending on the type of sensor, the resistance will either increase or decrease. In negative temperature coefficient (NTC) sensors, the internal resistance will decrease as the temperature rises (and vice versa). In positive temperature coefficient (PTC) sensors, the opposite is true and resistance will increase with rising temperature. Most automotive coolant temperature sensors are NTC sensors. The engine control unit (ECU) sends out a regulated reference voltage (typically 5 volts) to the coolant temperature sensor. The voltage drop across the sensor will change according to the temperature because its resistance changes. The ECU is then able to calculate the temperature of the engine, and then (with inputs from other engine sensors) uses lookup tables to carry out adjustments to the engine actuators, i.e. change the fuel injection or ignition timing.

The vehicle coolant flow and coolant quality sensor assembly 10 further includes a printed circuit board (PCB) 36 including one or more of a microcontroller and a transceiver (wireline and/or wireless) coupled to one or more of the coolant flow sensor, the coolant quality sensor, and the coolant temperature sensor. The vehicle coolant flow and coolant quality sensor assembly 10 still further includes an electronic connector 38 coupled to the PCB 36.

The benefit of better monitoring and understanding coolant flow in a vehicle is multifaceted. Early detection of coolant and thermal management system failure gives an operator more time to respond accordingly, preventing damage to a battery pack, for example. Further, appropriate thermal management of the battery pack increases the longevity of the battery pack. By better understanding the flow of the coolant circuit, it is possible to increase the range of a vehicle by running a coolant pump less or at a reduced rate when excess thermal management is not needed. Further, determining coolant system degradation can push consumers to service their coolant systems instead of relying on maintenance schedules.

The placement of the vehicle coolant flow and coolant quality sensor assembly 10 may be substantially adjacent to the following components: the charge port connector, the fast charge contactor assembly, the coolant line to the power conversion system (PCS), the PCS 54 itself, the high voltage controller (HVC), the low voltage connector to the HVC, the 12V output from the PCS, the positive high voltage (HV) power switch, the coolant line to the PCS, the HV connector to the cabin heater and compressor, the cabin heater/compressor/PCS direct current (DC) output fuse, the HV connector to the rear drive unit, the HV pyro fuse, the HV connector to the front drive unit, the negative HV power switch, the connector for three phase alternating current (AC) charging, etc.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims for all purposes.

What is claimed is:

1. A vehicle coolant flow and coolant quality sensor assembly, comprising:
    a housing defining a coolant flow channel communicating coolant from a first port to a second port;
    a coolant flow sensor disposed partially within the coolant flow channel and contacting the coolant, wherein the coolant flow sensor is operable for measuring flow of the coolant; and
    a coolant quality sensor disposed partially within the coolant flow channel and contacting the coolant, wherein the coolant quality sensor is operable for measuring ability to absorb heat of the coolant;
    wherein the coolant flow sensor and the coolant quality sensor are each partially disposed conformally within a widened portion of the housing adjacent to the coolant flow channel.

2. The vehicle coolant flow and coolant quality sensor assembly of claim 1, further comprising a coolant temperature sensor disposed partially within the coolant flow channel and contacting the coolant, wherein the coolant temperature sensor is operable for measuring temperature of the coolant, wherein the coolant temperature sensor is partially disposed conformally within the widened portion of the housing adjacent to the coolant flow channel.

3. The vehicle coolant flow and coolant quality sensor assembly of claim 1, wherein the coolant flow sensor comprises a dual coil magnetic flow meter.

4. The vehicle coolant flow and coolant quality sensor assembly of claim 1, wherein the coolant quality sensor comprises a sealed hot wire anemometer.

5. The vehicle coolant flow and coolant quality sensor assembly of claim 1, further comprising a printed circuit board comprising one or more of a microcontroller and a transceiver coupled to one or more of the coolant flow sensor and the coolant quality sensor, wherein the printed circuit board is disposed conformally within the widened portion of the housing adjacent to the coolant flow channel.

6. The vehicle coolant flow and coolant quality sensor assembly of claim 5, further comprising an electronic connector coupled to the printed circuit board.

7. The vehicle coolant flow and coolant quality sensor assembly of claim 1, further comprising a sealing member disposed about one or more of the first port and the second port.

8. The vehicle coolant flow and coolant quality sensor assembly of claim 1, wherein the housing is disposed in a cooling and thermal management system of one of an internal combustion engine (ICE) vehicle, a hybrid vehicle, and an electric vehicle.

9. The vehicle coolant flow and coolant quality sensor assembly of claim 1, wherein the vehicle coolant flow and coolant quality sensor assembly is used to monitor coolant used to cool one or more of an engine, a motor, a transmission, a battery pack, and high power electronics.

10. The vehicle coolant flow and coolant quality sensor assembly of claim 1, wherein the vehicle coolant flow and coolant quality sensor assembly is operable for alerting a user to one or more of coolant flow below a predetermined threshold, coolant ability to absorb heat below a predetermined threshold, and coolant temperature above a predetermined threshold.

11. A method for providing a vehicle coolant flow and coolant quality sensor assembly, comprising:
    providing a housing defining a coolant flow channel communicating coolant from a first port to a second port;
    providing a coolant flow sensor disposed partially within the coolant flow channel and contacting the coolant, wherein the coolant flow sensor is operable for measuring flow of the coolant;
    providing a coolant quality sensor disposed partially within the coolant flow channel and contacting the coolant, wherein the coolant quality sensor is operable for measuring ability to absorb heat of the coolant; and
    disposing the housing in a cooling and thermal management system of a vehicle;

wherein the coolant flow sensor and the coolant quality sensor are each partially disposed conformally within a widened portion of the housing adjacent to the coolant flow channel.

12. The method of claim 11, further comprising providing a coolant temperature sensor disposed at least partially within the coolant flow channel and contacting the coolant, wherein the coolant temperature sensor is operable for measuring temperature of the coolant, wherein the coolant temperature sensor is partially disposed conformally within the widened portion of the housing adjacent to the coolant flow channel.

13. The method of claim 11, wherein the coolant flow sensor comprises a dual coil magnetic flow meter.

14. The method of claim 11, wherein the coolant quality sensor comprises a sealed hot wire anemometer.

15. The method of claim 11, further comprising providing a printed circuit board comprising one or more of a microcontroller and a transceiver coupled to one or more of the coolant flow sensor and the coolant quality sensor, wherein the printed circuit board is disposed conformally within the widened portion of the housing adjacent to the coolant flow channel.

16. The method of claim 15, further comprising providing an electronic connector coupled to the printed circuit board.

17. The method of claim 11, further comprising providing a sealing member disposed about one or more of the first port and the second port.

18. The method of claim 11, wherein the housing is disposed in the cooling and thermal management system of one of an internal combustion engine (ICE) vehicle, a hybrid vehicle, and an electric vehicle.

19. The method of claim 11, wherein the vehicle coolant flow and coolant quality sensor assembly is used to monitor coolant used to cool one or more of an engine, a motor, a transmission, a battery pack, and high power electronics.

20. The method of claim 11, wherein the vehicle coolant flow and coolant quality sensor assembly is operable for alerting a user to one or more of coolant flow below a predetermined threshold, coolant ability to absorb heat below a predetermined threshold, and coolant temperature above a predetermined threshold.

* * * * *